United States Patent [19]

Adler-Nissen et al.

[11] Patent Number: 4,478,939

[45] Date of Patent: Oct. 23, 1984

[54] SPS, SPS-ASE AND METHOD FOR PRODUCING SPS-ASE

[75] Inventors: Jens L. Adler-Nissen, Gentofte; Henrik Gürtler, Lyngby; Georg W. Jensen, Bagsvaerd; Hans A. S. Olsen, Vanløse; Steen Riisgaard, Vaerløse; Martin Schülein, Copenhagen, all of Denmark

[73] Assignee: Novo Industri A/S, Denmark

[21] Appl. No.: 334,329

[22] Filed: Dec. 24, 1981

[51] Int. Cl.$^3$ ............... C12N 9/24; C12N 9/40; C12N 9/42; C07G 17/00; A23J 1/14; A23L 2/34

[52] U.S. Cl. .................... 435/200; 435/208; 435/209; 435/262; 435/267; 435/272; 435/274; 435/275; 426/44; 426/46; 426/49; 426/51; 426/52

[58] Field of Search ............ 435/200, 208, 209, 262, 435/267, 272, 274, 275; 426/44, 46, 49, 51, 52

[56] References Cited

U.S. PATENT DOCUMENTS 3,484,255 12/1969 Okada et al. .............. 435/200 X
3,640,723 2/1972 Uhlig et al. ............... 426/46
4,119,733 10/1978 Hsieh et al. ............... 426/46

OTHER PUBLICATIONS

Derwent Abstract 60536 C/35, (1980), of Belgian Patent No. 882,769.
Kawai et al., Agricultural and Biological Chemistry, vol. 43(9), 1855–1862, (1979).
Research Disclosure 19314, May, 1980.

*Primary Examiner*—Lionel M. Shapiro
*Attorney, Agent, or Firm*—Fidelman, Wolffe & Waldron

[57] ABSTRACT

SPS—A novel pectic-like polysaccharide derived from soy plant cell walls characterized by capability to bind to proteins.

SPS-ase—The carbohydrase complex capable of decomposing SPS into decomposition products incapable of attaching to protein, and method for producing SPS-ase by cultivation of an SPS-ase producing microorganism for which preferred microorganism strains are *Aspergillus aculeatus* CBS 101.43 and *Aspergillus japonicus* IFO 4408.

7 Claims, 16 Drawing Figures

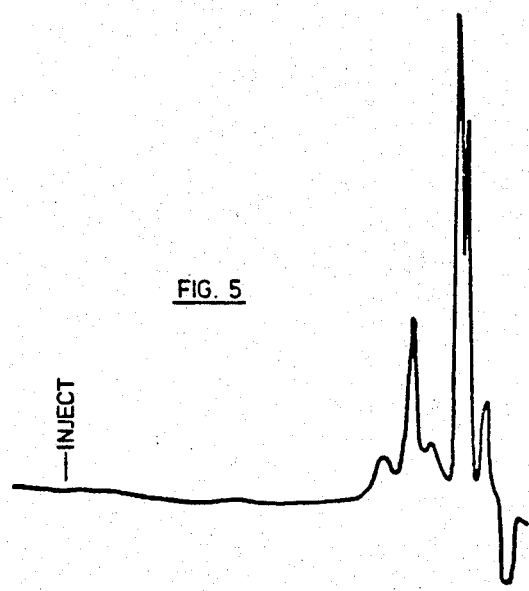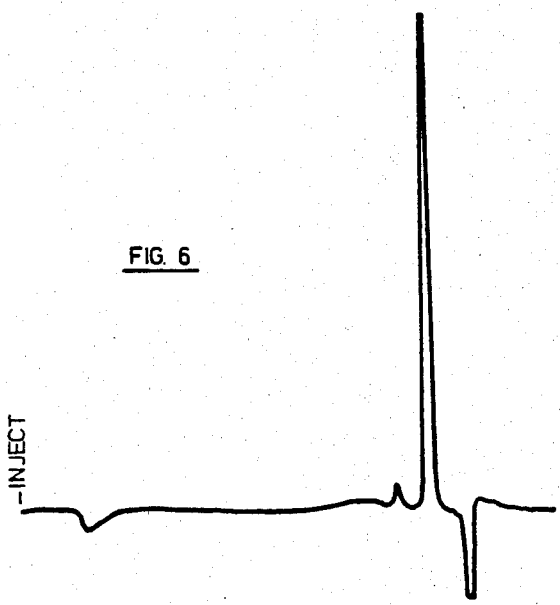

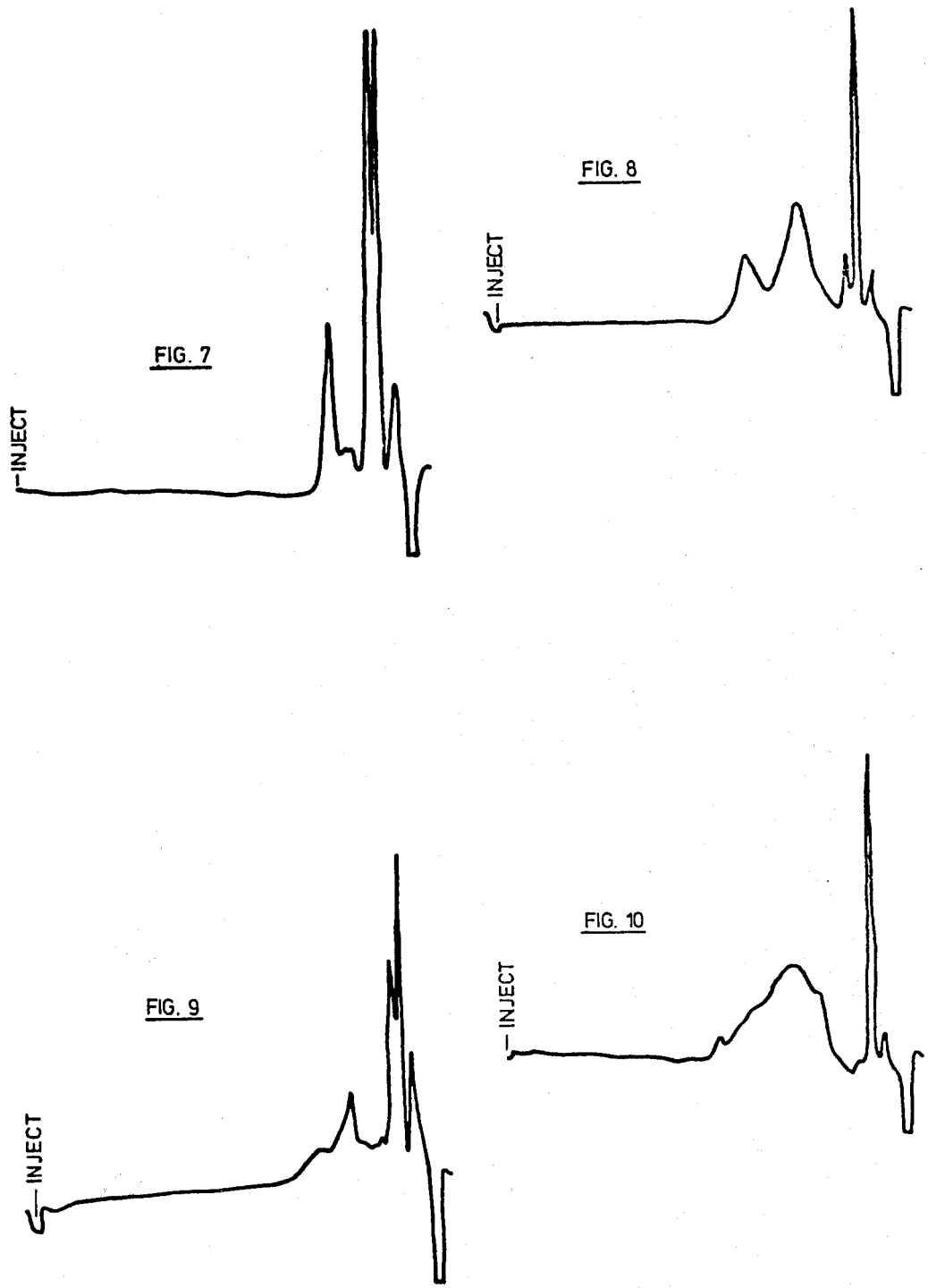

SPS, SPS-ASE AND METHOD FOR PRODUCING SPS-ASE

Improvements in and relating to a novel enzyme complex capable of decomposing SPS, a high molecular weight polysaccharide, the isolated SPS, and a method for production of such enzyme.

INTRODUCTION

A method for production of a purified vegetable protein product (pvp) by enzymatic removal of the remanence, without dissolution and reprecipitation of the protein, is described in Belgian Pat. No. 882,769. The purity of the pvp obtainable by the known method is not satisfactory and therefore open to improvement. In the examples, a purity of the pvp of about 85% was demonstrated.

The art has recognized that the remanence or non-protein (also non-starch, non-oil, etc.) ingredients associated with vegetable materials like seeds, beans, nuts, etc., including soybeans, grape seeds, cotton seeds, sunflower seeds, faba beans, peas and peanuts constitutes a mixture containing the following polysaccharides:
  (1) Pectic-like polysaccharides mainly consisting of
      D-galacturonic acid, D-galactose, L-arabinose,
      D-xylose, and L-rhamnose
  (2) Hemicelluloses
  (3) Cellulose However, even though vegetable materials, notably soy protein forms, have been treated with enzyme compositions containing pectinase, hemicellulase, cellulase, a substantial proportion of the remanence has remained with the protein.

RATIONALE OF THE INVENTION

The present invention is based upon the surprising discovery that a certain part of the remanence released from the vegetable matter substrate, e.g., soymeal, by the enzymatic action of carbohydrases is a hitherto unreported water soluble pectic-like polysaccharide that does not separate from the vegetable protein. Presence of this polysaccharide is a principal reason for the relatively low protein content in pvp made with enzymatic treatment, i.e., less than 90% for soy pvp.

Thus, one object of this invention is to isolate this water soluble pectic-like polysaccharide, hereinafter denominated SPS.

A second object of this invention is to employ SPS for discovery of microorganisms which elaborate enzymes that degrade SPS.

A third object of this invention is to provide an enzyme complex that degrades SPS, such enzymes or groups of enzyme activities being hereinafter denominated SPS-ase.

A fourth object of this invention is to provide a method for producing SPS-ase.

Employment of SPS-ase for conversion of vegetable material such as soymeal into pvp results in higher protein content pvp than could be recovered heretofore from enzymatic treatment. Reference is made to companion application, Ser. No. 339,330, filed concurrently herewith for the details of an SPS-ase containing enzyme composition agent suited to treatment of soy meal, soy flour, etc., and to the method of converting soy meal, soy flour, etc., into pvp. Other uses to which SPS-ase is suited will be discussed hereinafter.

SPS which will be described in detail hereinafter is a polysaccharide characterized by an ability to attach itself to proteins of animal and plant origin, forming a gel or a precipitate. SPS can be used to recover or simply remove protein from aqueous solution.

BRIEF STATEMENT OF THE INVENTION

The foregoing objects have all been achieved. In short this invention comprises:

SPS—The water soluble polysaccharide which binds to proteins, dissolved or in solid form. The molecular weight of SPS by HPLC gel filtration is between about $4.9 \times 10^4$ and $5 \times 10^6$, and is principally formed of residues of galacturonic acid, rhamnose, galactose, and xylose and fucose.

SPS-ase—The enzyme complex capable of decomposing SPS at least sufficiently to remove protein binding capability.

DISCUSSION OF THE INVENTION

For understanding of the discussion of this invention hereinafter provided, reference will be made to the attached drawing, wherein:

FIG. 4 is the SPS chromatogram.

FIG. 5 is the chromatogram of SPS after treatment with SPS-ase.

FIG. 6 is the chromatogram of the SPS solution used to generate FIG. 4 after incubation with soy protein.

FIG. 7 is the chromatogram of the solution used to generate FIG. 5 after incubation with soy protein.

FIG. 8 is the chromatogram of APS (acidic polysaccharide from soy sauce) after treatment with Pectolyase TM.

FIG. 9 is the chromatogram of APS treated with SPS-ase.

FIG. 10 is the chromatogram of SPS treated with Pectolyase TM.

SPS

Figure 1:
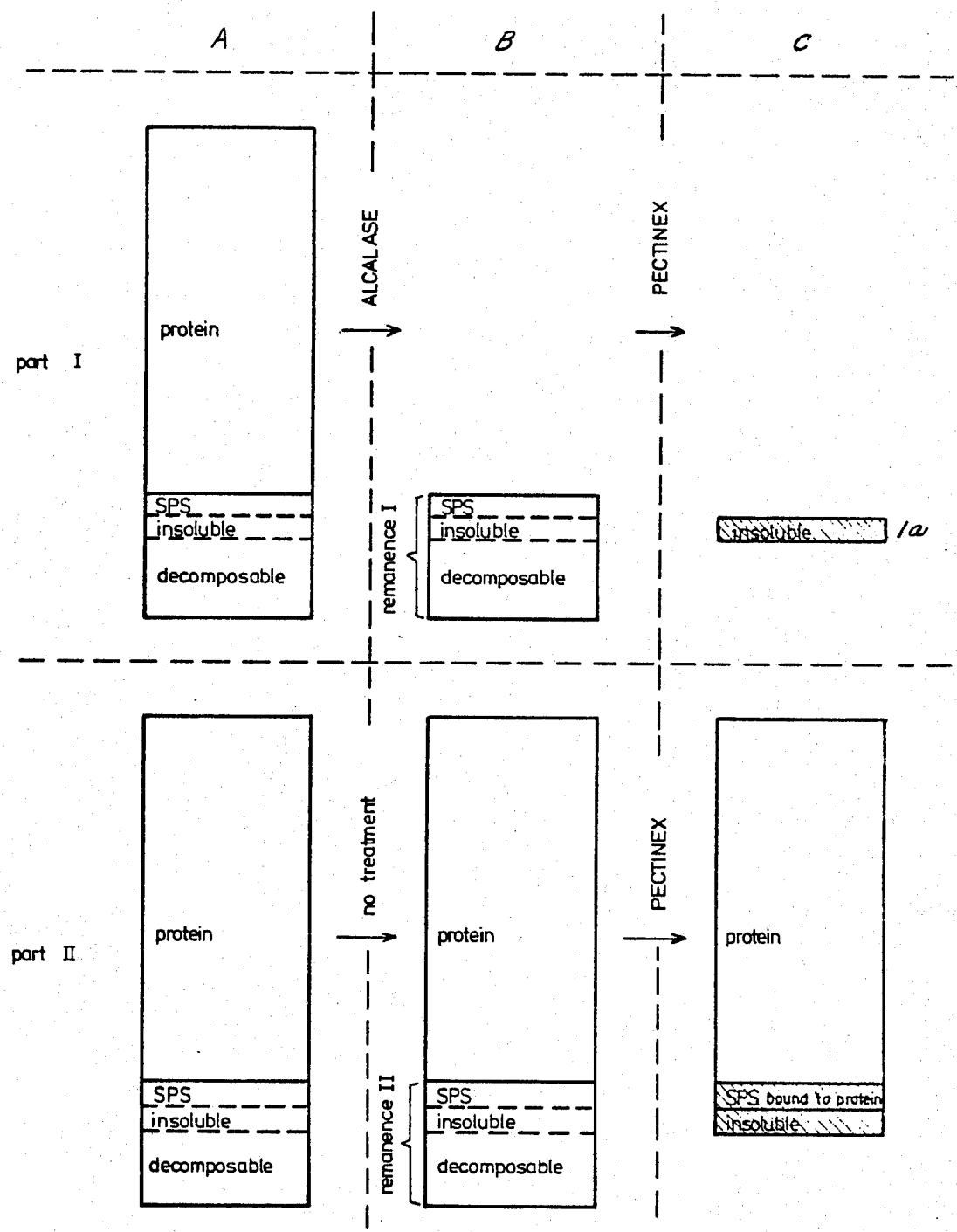
FIG. 1 is a pictorial representation of test results evidencing existence of SPS.

In plant tissue, e.g., soybeans, pectic polysaccharides, hemicelluloses and celluloses are interlinked into a matrix structure in the cell walls. In plant cells, the bulk of the protein is not associated with the cell wall. The same is true of oil and starch content if present. Normal processing to recover oil, protein, etc., e.g., pressing, extraction, etc. release the ingredients such as oil and protein not associated with the cell wall but the cell wall polysaccharide matrix is left largely intact. Treatment with carbohydrases such as pectinases, hemicellulases and cellulases degrades the polysaccharide matrix releasing fragments of varying molecular weight and properties. Not all of the polysaccharide material is solubilized. Treatment of soy meal with the hitherto known pectinase containing carbohydrases releases a high molecular weight fraction of the pectic polysaccharide component in the cell wall matrix not previously described in the art that interferes with recovery of a pvp containing more than 90% protein. Such a pectic polysaccharide has now been isolated.

The existence of the discrete hitherto unrecognized polysaccharide component denominated SPS can be demonstrated by treating soy meal in a manner that separates all polysaccharides from the protein, then treating the polysaccharides so as to isolate the SPS; all as is described below by way of the following Example.

EXAMPLE 1

A charge of soy meal was treated in aqueous suspension at pH 8 with ALCALASE$^R$ 0.6 L (NOVO INDUSTRI A/S) a proteinase from *B. licheniformis*, for about four hours at 50° C., using one Anson Unit of enzyme per 100 gms of soy meal. The enzymatically degraded solubilized proteins were removed, leaving the remanence in solid form.

The remanence was then treated in aqueous suspension with a commercial pectinase (PECTINEX TM —NOVO INDUSTRI A/S) and the undissolved remanence portion (1a) removed and weighed.

A like charge of soy meal was treated only with the pectinase, which treatment left the protein in solid form, along with any remanence fractions not solubilized by the pectinase treatment. Analysis of the pectinase treated soy meal showed a polysaccharide content therein exceeding the undissolved remanence fraction (1a).

When the carbohydrate containing supernatant remaining after pectinase treatment of the remanence and removal of the undissolved remanence fraction (1a) is brought together with a soy protein suspension, some polysaccharide disappears from the solution.

The results can be described as follows with reference being made to FIG. 1 of the attached drawing whereon the results of Example 1 are shown; only materials existing as undissolved solids are indicated, all supernatants being left out. The total charge of soy meal divided in two equal parts, part I and part II (Column A in FIG. 1) is shown with Part I decomposed proteolytically at a pH value of about 8 by means of AL-CALASE ®0.6 L. After washing at around pH 8 in order to eliminate the protein, the remanence was separated from the supernatant and washed. In this way, the pure remanence (designated Remanence I) was isolated (Column B, FIG. 1). For the sake of clarity, the remanence in Part II of the soy meal which was not treated has been designated Remanence II (Column B, FIG. 1). When Remanence I and all of Part II are decomposed by a commercial pectinase, e.g., PECTINEX TM, it is found that the undissolved part of Remanence I is much smaller than the undissolved part of Remanence II, on the basis of nitrogen and dry matter mass balances, vide FIG. 1, where the hatched areas in Column C correspond to the insoluble, non-protein materials.

That some discrete unusual fraction of the remanence has been solubilized by the treatment given Part I of the soy meal has been demonstrated (by bringing the supernatant from the pectinase treated Remanence I together with a soy protein suspension at pH 4.5, whereupon polysaccharide disappears from solution). This discrete polysaccharide fraction in the supernatant from Remanence I, i.e., the part of the remanence decomposition product, soluble in water in the absence of soy protein, but bound to soy protein at or around the isoelectric point of soy protein, if soy protein is present, has been designated SPS (Soluble Polysaccharide), vide FIG. 1.

The SPS has a molecular weight distribution between $5 \times 10^6$ and $4.9 \times 10^4$ by HPLC gel filtration chromatography and may be recovered by treating Remanence I with pectinase as described above, then subjecting the (supernatant) solution to ultrafiltration to remove oligosaccharides, leaving the SPS in the retentate. The SPS may, if desired, be precipitated from the retentate by addition of ethanol.

PRODUCTION OF SPS

As previously mentioned, the starting material for production of SPS is soy remanence.

Figure 2:
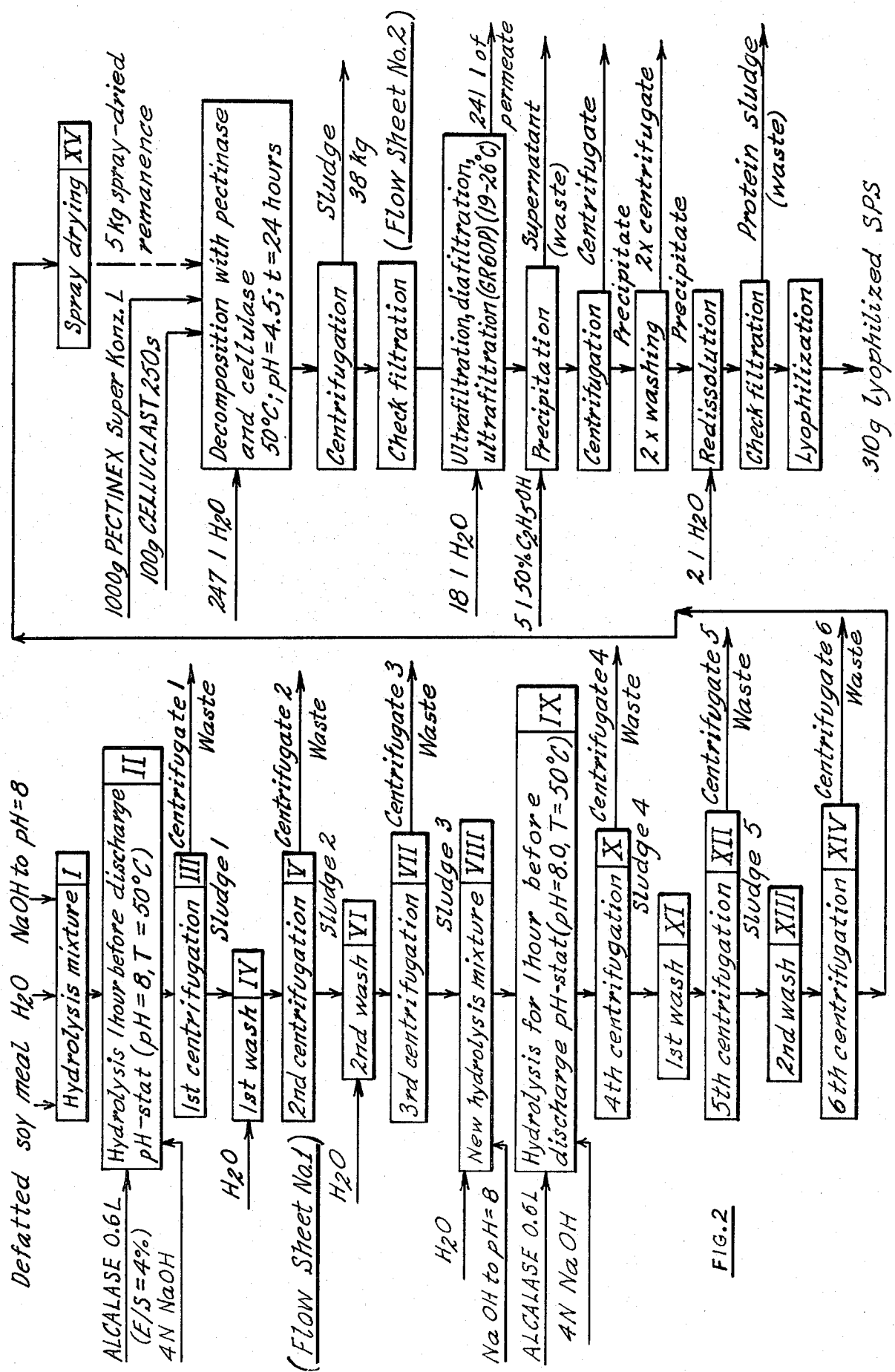
FIG. 2 is a flow sheet illustration of the process for isolating SPS.

Soy remanence is the protein free carboyhydrate material (which in practice often contains minor amounts of lignin and minerals) in defatted and dehulled soy meal, which carbohydrate material is insoluble in a aqueous medium at pH 4.5, and it can be separated from the protein as is illustrated by FIG. 1 and in more detail by Flow sheets 1 and 2 of FIG. 2 so as to recover SPS.

Referring now to the Flow Sheets, defatted soy meal (Sojamel 13 from Aarhus Oliefabrik A/S) is suspended in deionized water of 50° C. in a weight proportion soy meal:water = 1:5 in a tank with pH-stat and temperature control. pH is adjusted to 8.0 with 4N NaOH (I). A pH-state hydrolysis is performed with about 2 grams of ALCALASE ®0.6 L (a proteolytic enzyme from *B. licheniformis* with an activity of 0.6 Anson units/g, determined according to the Anson method described in NOVO ENZYME INFORMATION IB No. 058 e-GB), per 100 gm of soy meal. The ratio enzyme/substrate should equal 4% of the protein in the soy meal (II). After a hydrolysis of 1 hour the sludge is separated by centrifugation (III) and washing (IV); this operation is performed twice (V, VI, VIII). The treated sludge is hydrolyzed once more for 1 hour with the same quantity of ALCALASE ®0.6 L as used previously (VIII, IX). Then the sludge is separated by centrifugation (X) and washed twice (XI, XII, XIII, XIV), after which the final washed sludge (6) is spray-dried (XV). The spray-dried powder is the total soy remanence and serves as a raw material for the production of SPS.

SPS is the water soluble polysaccharide fraction formed by treatment of the soy remanence with pectinase containing carbohydrases. The SPS is produced from the remanence and isolated in the following manner by the reaction sequence illustrated in Flow Sheet 2 of FIG. 2 and described below.

1. The soy remanence is diluted with water to a 2% dry matter suspension and kept in suspension at 50° C. with temperature control.

2. The pH value is adjusted to pH 4.5 with 6N NaOH.

3. PECTINEX TM Super conc. L (Schweizerische Ferment AG, Basle, Switzerland) is added in an amount of 200 g/kg dry matter, and also CELLU-CLAST TM 200 L (NOVO INDUSTRI A/S) is added in an amount of 20 g/kg dry matter.

4. The contents of the tank are stirred at 50° C. for 24 hours.

5. The enzymes are inactivated by raising the pH to 9.0 with 4N NaOH. The reaction mixture is held for 30 minutes, and the pH-value is then readjusted to 4.5 with 6N HCl.

6. The reaction mixture is centrifuged and both centrifugate and sludge are collected.

7. The centrifugate from step 6 is check filtered on a filter press (the filter is washed with water before check filtration).

8. The check filtrate is ultrafiltered, diafiltered and again ultrafiltered on a membrane with a cutoff value of 30,000 (DDS GR 60-P from De Danske Sukkerfabrikker), according to the following:

A. Ultrafiltration corresponding to a volume concentration of 6.

B. Diafiltration until the percentage of dry matter in the permeate is 0 (~0° Brix).

C. Ultrafiltration to around 15% dry matter in the concentrate.

The temperature is 50° C., pH is 4.5 and the average pressure is 3 bar.

9. The ultrafiltered concentrate is cooled to 5° C. and an equal volume of 96% ethanol is added.

10. The precipitate is collected by means of a centrifuge.

11. The precipitate is washed twice with 50% v/v ethanol in H$_2$O, corresponding to the volume of centrifugate from step 10, i.e., two centrifugations are performed.

12. The washed precipitate is redissolved in water with a volume which equals the volume of the ultrafiltered concentrate from step 9.

13. The liquid from step 12 is check filtered on a glass filter.

14. The clear filtrate which contains pure isolated SPS is lyophilized.

CHARACTERIZATION OF SPS

The tests and results hereinafter described may be summarized as follows:

By gel chromatography on HPLC equipment (Waters pump mode 6000, Waters data module 730, and Waters refractometer R 401) the molecular weight distribution of the isolated SPS has been determined and is shown on FIG. 4. By the same method the molecular weight distribution of the decomposition products of SPS hydrolyzed by SPS-ase has been determined and is illustrated in FIG. 5. Furthermore, the binding effect between soy protein and SPS is illustrated by FIG. 6 and the absence of binding effect between soy protein and SPS decomposed by SPS-ase is illustrated by FIG. 7.

Figure 3:
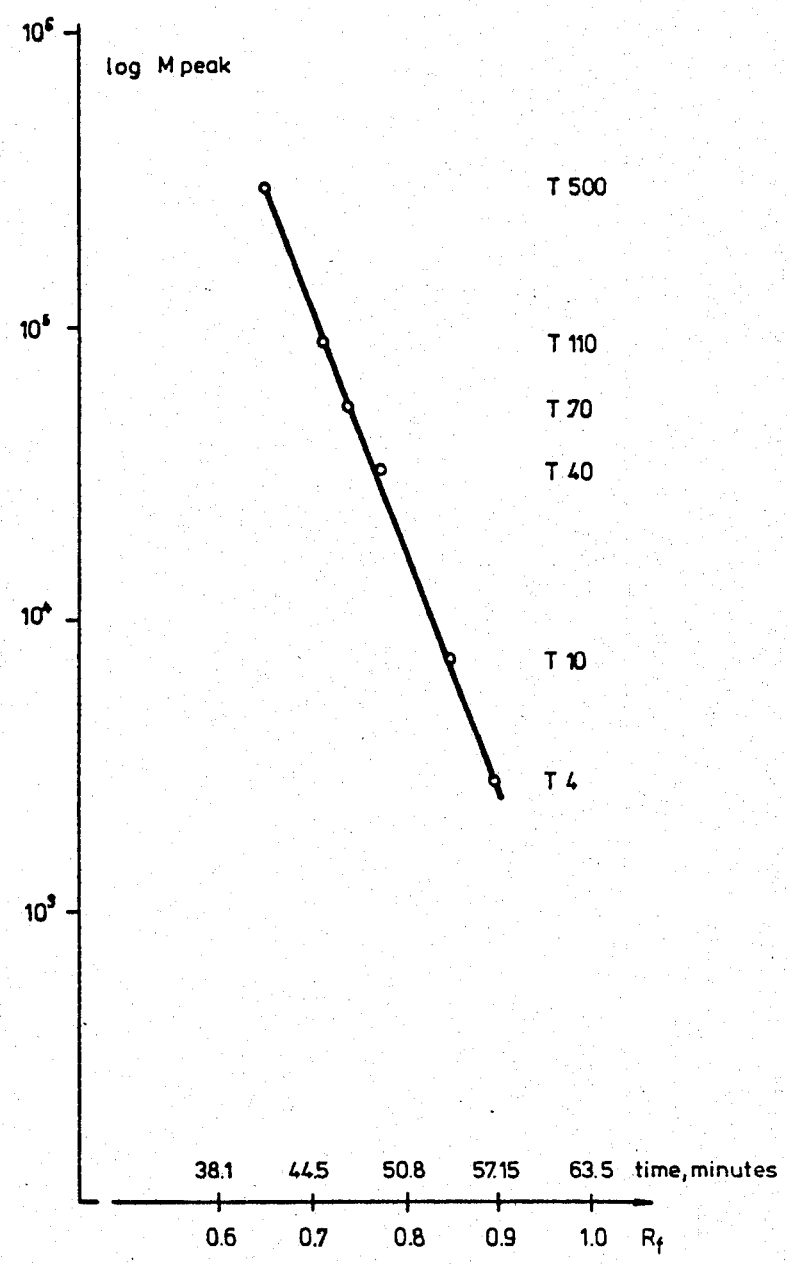
FIG. 3 is a graph showing the calibration curve for HPLC gel filtration chromatography.

The calibration curve (the logarithm of the molecular weight plotted against $R_f$, where the $R_f$-value for glucose is arbitrarily defined as 1 and the $R_f$-value for a specific dextran is defined as the retenion time for this dextran divided by the retention time for glucose) has been established by several standard dextrans with known molecular weights (T 4, T 10, T 40, T 70, T 110, T 500) Pharmacia Fine Chemicals AB, Uppsala, Sweden. The $R_f$-value for the maximum of each dextran peak has been found, and the corresponding molecular weight has been calculated as $\sqrt{\overline{M}_w \cdot \overline{M}_n}$, is the average value of the molecular weight according to weight and $\overline{M}_n$ is the average value of the molecular weight according to number. As an eluent for this chromatographic procedure 0.1M NaNO$_3$ has been used. The columns used in the chromatographic procedure are 60 cm PW 5000 followed by 60 cm PW 3000 from Toyo Soda Manufacturing Co., Japan. In this manner the relationship between molecular weight and $R_f$ for the above-indicated dextrans has been established, and is illustrated by FIG. 3.

From the chromatogram shown in FIG. 4 the calculated molecular weight distribution of SPS averages a value of $\overline{M}_w$ of around $5.4 \times 10^5$ and a value of $\overline{M}_n$ of around $4.2 \times 10^4$. The chromatogram exhibits two distinct peaks at retention time 34.5 minutes (6%) corresponding to a molecular weight of around $5 \times 10^6$ and retention time 47.12 minutes (67%) corresponding to a molecular weight of around $4.9 \times 10^4$. Also, this curve shows a shoulder between these two peaks at retention time 41.25 minutes (27%) corresponding to a molecular weight of $2.8 \times 10^5$.

After decomposition of SPS in solution with SPS-ase the hydrolysis mixture was membramne filtered, and the filtrate was chromatographed. It was found that around 55% of SPS is decomposed to mono-, di- and triasccharides, and that the remaining 45% are decomposed to a polymer with three peaks with the following molecular weights: $5 \times 10^4$, $10^4$ and $4.4 \times 10^3$, as can be seen in the chromatogram of FIG. 5.

In order to demonstrate both the binding effect between soy protein and SPS and the substantial reduction in the binding effect between soy protein and SPS decomposed by SPS-ase the following experiments have been performed.

3% SPS in 0.10M acetate buffer at pH 4.5 is added to a slurry of soy isolate (Purina E 500) to generate a suspension with a ratio isolate/SPS of 10:1. This suspension is incubated for 18 hours on a shaking bath at 50° C. After incubation the suspension is centrifuged, and the clear supernatant is analyzed on the HPLC unit previously described. From FIG. 6 as compared to FIG. 4 it can be seen that the SPS is completely adsorbed by the soy isolate.

The procedure is repated with a 3% SPS solution hydrolyzed by SPS-ase from CBS 101.43 and the chromatogram shown as FIG. 7. A comparison of FIG. 7 to FIG. 5 shows that no compound in the hydrolyzed SPS solution of molecular weight below about $10^4$ is adsorbed by the soy isolate.

Hydrolysis of SPS has eliminated the protein binding capability in a practical sense. Only 10-15% of the carbohydrate that had been part of SPS adsorbs to the soy isolate. Characterization of SPS-ase as removing the protein binding capability is then more reasonable than characterization as reducing such capability.

An NMR-analysis of the SPS reveals the following approximate composition of the SPS:

(1) alpha-galacturonic acid, approximately 45%, with about 40% of the total amount of alpha-galacturonic acid present as the methyl ester;

(2) rhamnopyranose and fucopyranose, approximately 20%;

(3) galactopyranose, approximately 15%, and (4) beta-xylopyranose, approximately 20%.

The above named constituents are believed to be in a structure of a rhamnogalacturonic backbone and side chains of xylose, galactose, and fucose.

Complete acid hydrolysis of SPS (8 hours in 1N H$_2$SO$_4$) and subsequent TLC analysis indicated also the presence of minor amounts of arabinose in fully hydrolyzed SPS.

An HPLC analysis of the SPS decomposed by the SPS-ase enzyme complex from CBS 101.43 shows a considerable reduction in molecular weight. The NMR-spectrum shows that most of the methyl ester groups have disappeared and also that the content of xylose and galactose in the higher molecular weight mateials has decreased. The NMR-spectrum taken of the part of the SPS decomposition product which precipitation on addition of one volume of ethanol to one volume of SPS decomposition product is similar to the NMR-spectrum of the SPS, with the above indicated modifications, concerning the ester groups and the content of xylose and galactose.

UNIQUENESS OF SPS

So far as the inventors hereof have been able to ascertain SPS is a discrete unique fragment of the soy remanence, different from other high molecular weight polysaccharides obtained heretofore from soybeans or soy remanence. The most closely related of the polysaccharides described in the literature are believed to be acid polysaccharide (APS), (see Agr. Biol. Chem. Vol. 36, No. 4, pp. 544–550 [1972]), and rhamnogalacturonan-I (see Pure and Applied Chemistry Vol. 53, pp. 79–88 [1981]).

The latter which has not been investigated, may be one component in SPS or a large fragment of SPS molecules. Differences in composition exist. For example, rhamnogalacturonan-I does not contain xylose and fucose and does contain more arabinose than is in SPS.

APS has been investigated and below is shown to be different from SPS.

APS was prepared as indicated in Agr. Biol. Chem., Vol. 36, No. 4, p. 554–550 (1972).

The HPLC gel filtration chromatograms of SPS and APS are clearly different.

APS and SPS were hydrolyzed by an SPS-ase (KRF-68) and PECTOLYASE ™ by treatment of 25 ml solution of either 2% APS or 2% SPS in 0.1M acetate buffer of pH 4.5 with 10 mg KRF 68 or 30 mg PECTOLYASE ™. KRF 68 is an SPS-ase preparation hereinafter described in Example 1, whereafter the decomposition mixture was gel chromatographed on the HPLC equipment.

The results are tabulated below.

| Polysac-charide | Enzyme | HPLC gel chromato-gram | Polysaccharide Decomposed | Not decomposed |
|---|---|---|---|---|
| APS | Pectolyase | FIG. 8 | x | |
| APS | KRF 68 | FIG. 9 | x | |
| SPS | Pectolyase | FIG. 10 | | x |
| SPS | KRF 68 | FIG. 5 | x | |

SPS can be and has been employed for screening of microorganisms to discover strains capable of elaborating an enzyme, i.e., SPS-ase, that decomposes SPS. In addition, SPS solutions have been tested for their coagulating ability against aqueous suspensions or solutions of animal and vegetable proteins. For example, mixing serum albumin and a solution of SPS generated a precipitate, showing then that SPS can be employed to remove proteins from an aqueous suspension or solution thereof.

SPS-ASE PRODUCING MICROORGANISMS

Microorganisms to be tested for production of SPS-ase are each incubated on an agar slant substrate with a composition which enables growth of the microorganism. After initial growth on the agar slant substrate the microorganism is transferred to a liquid main substrate, in which the main carbon source is isolated SPS along with standard nutrients including nitrogen containing compounds, and the necessary salts and vitamins, preferably in the form of yeast extract. The composition of the main substrate depends, of course, upon the growth requirements of the microorganism, the guiding principal being that the main substrate should be able to support growth and metabolism of the microorganism. When growth has taken place for a suitable period of time, e.g., 1–7 days, depending upon the growth rate of the microorganism in question, a sample of the fermentation broth is analyzed for SPS-ase as will be described hereinafter.

Several SPS-ase producing microorganisms have been found. The first two microorganisms listed in the following table are SPS-ase producers. Also listed in the table is a strain belonging to the species *Aspergillus japonicus* which is not an SPS-ase producer, but which produces an enzyme capable of decomposing APS (see Agr. Biol. Chem., Vol. 40 (1), 87–92 [1976]).

| SPS-ase producer | | Species | | Our identifying designation | Official identifying designation | Deposition year |
|---|---|---|---|---|---|---|
| Yes | No | Asp. japo-nicus | Asp. acule-atus | | | |
| x | | | x | A 805 | CBS 101.43 | 1943 |
| x | | x | | A 1443 | IFO 4408 | 1950 |
| | x | x | | A 1384 | ATCC 20236 | 1969 |

A short identification of the above indicated strains can be found in the following culture catalogs:

List of Cultures 1978 Centraalbureau voor Schimmelcultures, Baarn, The Netherlands;

Institute for Fermentation Osaka, List of Cultures, 1972, 5th edition, 4–54, Juso-Nishinoch, Higashiyodogawa-ku, Osaka, Japan;

The American Type Culture Collection Catalogue of Strains I, 14th edition 1980, 12301 Parklawn Drive, Rockville, Md. 20852.

All the strains in the above indicated table correspond closely to the taxonomic description of the species *Aspergillus japonicus* and *Aspergillus aculeatus* appearing in The Genus Aspergillus of Raper and Fennell, 1965 (vide especially pages 327–330).

*Aspergillus aculeatus* and *Aspergillus japonicus* belong to the *Aspergillus niger* group. To date, no SPS-ase producers have been found outside the *Aspergillus niger* group and even in the *Aspergillus niger* group except for strains belonging to the species *Aspergillus aculeatus* and *Aspergillus japonicus*. Not all strains belonging to the species *Aspergillus aculeatus* and *Aspergillus japonicus* are SPS-ase producers.

These microorganisms produce more than one carbohydrase activity including pectolytic, cellulytic and hemicellulytic as well as an enzyme activity specific to SPS. However, the specific SPS activity separate and alone, degrades SPS only nominally. Yet a commercial pectinase and the isolated specific SPS activity degrade SPS to a great extent. (The same commercial pectinase alone does not degrade SPS). The SPS-ase enzyme complex of this invention comprises both the specific SPS-activity just described and a pectolytic activity. The SPS-ase containing enzyme mixture produced by *Aspergillus japonicus* IFO 4408 and *Aspergillus aculeatus* CBS 101.43 also exhibit hemicellulytic and cellulytic activity, both of which are desirable.

The SPS-ase of the invention is characterized by the fact that the enzyme complex herein termed SPS-ase is capable of decomposing SPS in an aqueous medium into decomposition products of which little will attach themselves to vegetable protein in the aqueous medium, far less than the SPS prior to decomposition would have attached itself to the same vegetable protein in the aqueous medium, e.g., less than 15%.

A preferred embodiment of the SPS-ase according to the invention is characterized by the fact that the SPS-ase is capable of decomposing soy SPS in an aqueous medium with a pH value not deviating more than 1.5 from 4.5 into decomposition products which in large measure do not attach themselves to soy protein in the aqueous protein.

A preferred embodiment of the SPS-ase according to the invention is the SPS-ase produced by *Aspergillus aculeatus* CBS 101.43. The same SPS-ase is produced by *Aspergillus japonicus* IFO 4408.

Since *Aspergillus aculeatus* CBS 101.43 also produces very potent cellulases, pectinases, and hemicellulases and proteinases besides the SPS-ase, the SPS-ase containing enzyme mixture produced by *Aspergillus aculeatus* CBS 101.43 is well suited as an agent for use for cell wall disintegration of vegetable materials. Thus, the enzyme mixture producible from *Aspergillus aculeatus* CBS 101.43 can be used in the food processing industry for treatment of fruit and vegetable mashes and for clarifying and viscosity reducing purposes in the processing of juice and wine. Also, the enzyme mixture can be used as a dewatering agent (i.e., an agent for decomposition of polysaccharides and hence for liberation of the water bound within the polymeric structure of the polysaccharides) in the processing of vegetables.

However, if the SPS-ase of *Aspergillus aculeatus* CBS 101.43 is intended for production of pvp as for example is described in the aforementioned companion application, the proteinase activity produced by this microorganism must be avoided, e.g., destroyed by deactivation as is hereinafter described.

FINGERPRINT OF SPS-ASE

A method designated the top-agar overlay technique has been developed for identification of individual components of an enzyme complex by crossed immunoelectrophoresis with a polyspecific antibody against all enzyme components in the enzyme complex. The method is based on the fact that enzymes are still active after the specific enzyme-antibody binding. The active enzyme site is not the site of the enzyme-antibody binding. The enzyme-antibody complexes precipitate as distinct arcs in the gel during the electrophoresis. Then the gel plate is covered with SPS dissolved in a top-agar. After heating to 45° C. for 20 hours in an atmosphere with a relative humidity of 100% the arc which possesses SPS-ase activity will appear as a clearing zone in the SPS top-agar cover after precipitation with a mixture of equal volume parts of ethanol and acetone when looked upon against a black background. Arcs which have no SPS-ase activity are left invisible.

Figure 11:
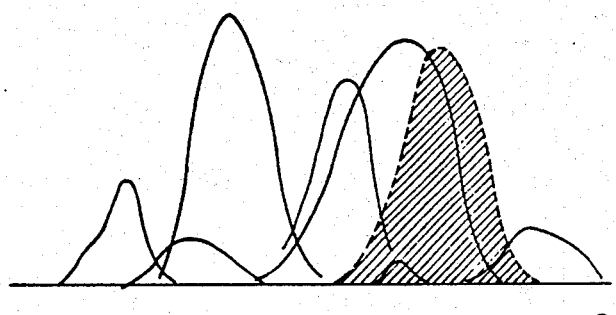
FIG. 11 is the immunoelectrophoretical fingerprint of the SPS-ase from *Aspergillus aculeatus* CBS-101.43.

Rabbits were immunized with the SPS-ase containing enzyme complex obtained by fermentation of *Aspergillus aculeatus* CBS 101.43, (KRF 68) and the polyspecific antibody was recovered. Using this polyspecific rabbit serum antibody a crossed immunoelectrophoresis of the same enzyme complex was performed, as described in H. H. Axelsen et al., "A Manual of Quantitative Immunoelectrophoresis", 6' printing 1977. Reference is now made to FIG. 11 which shows the arcs corresponding to different proteins produced by the microorganism. By means of the previously described top-agar overlay technique it was found that the hatched area corresponds to the specific enzyme activity against SPS. However, the hatched area has become visible only because the pectinase activity arc overlaps the SPS-activity arc. Thus, the hatched area also fingerprints the enzyme complex herein termed SPS-ase.

To guard against the possibility that a naturally occurring overlap in the enzyme (pectolytic and SPS activity) may not exist, the SPS containing agar topcover could include pectinase.

PURIFICATION OF SPS-ASE

The purification of SPS-ase preparations have been performed by ion exchange. The buffer is 50 mM Tris (trishydroxymethylaminomethane) which is adjusted to pH 7.0 with HCl. The column is K 50/30 from Pharmacia, Sweden. The ion exchange material is DEAE-trisacryl from LKB, Bromma, Sweden (300 ml). The flow rate is 100 ml/hour.

Figure 12:
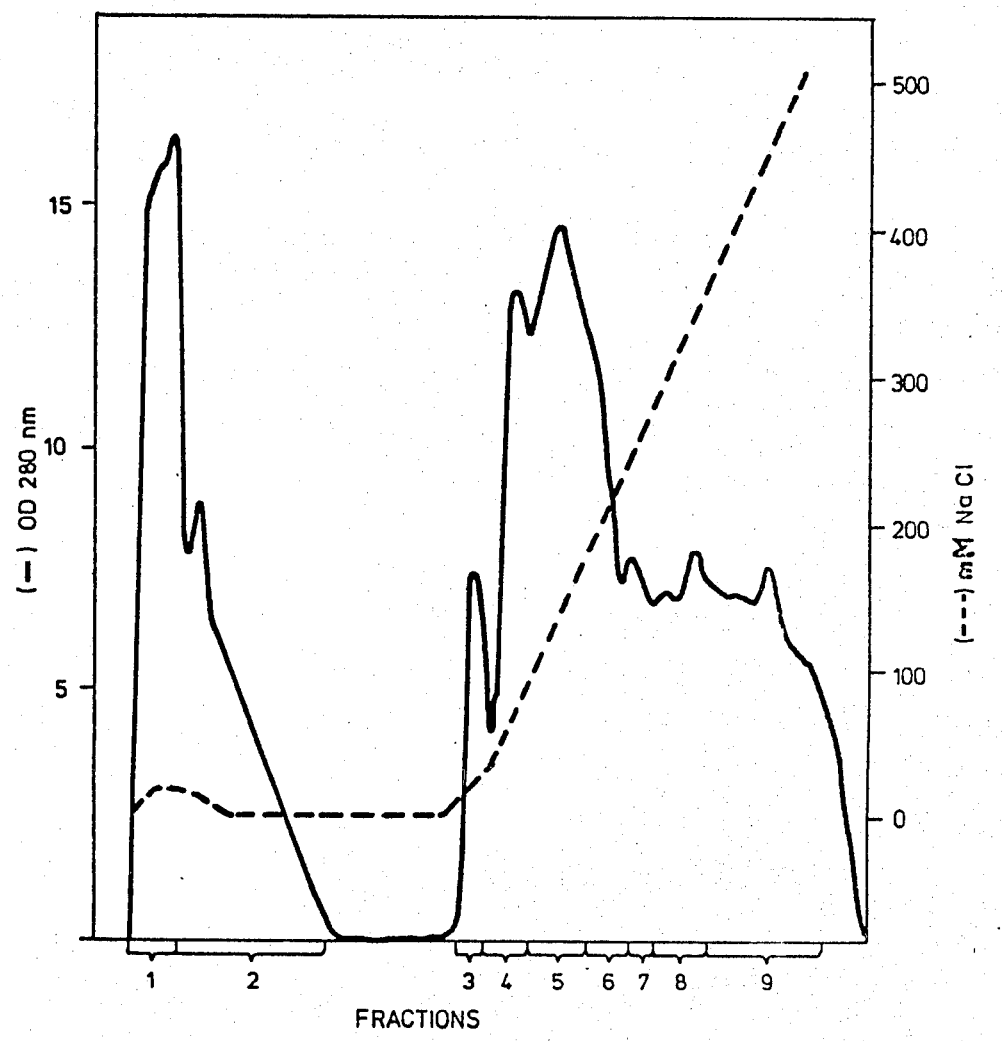
FIG. 12 is an ion-exchange chromatogram of the SPS-ase from *Aspergillus aculeatus* CBS-101.43.

For example, 15 g of the SPS-ase preparation KRF 92 was dissolved in 450 ml H$_2$O at 6° C., and all the following operations were carried out between 6° C. and 10° C. pH was adjusted to 7.0 with 1M Tris. The column was equilibrated with the buffer, and then the SPS-ase sample was introduced onto the column. OD$_{280}$ and the conductivity was measured on the eluate, reference now being made to the ion exchange chromatogram of FIG. 12. Fraction 1 is the eluate which is not bound to the ion exchange material. Then the column is washed with 2000 ml buffer which gives rise to fraction 2. Then a 0-500 mM NaCl gradient is established, giving rise to fractions 3-9. All nine fractions were concentrated to 200 ml and dialyzed against water to a conductivity of 2 mSi by dialysis (Hollow Fiber DP 2 from Amicon, Mass., U.S.A.). Then the nine fractions were freeze dried. Only fractions 1 and 2 exhibited activity against SPS.

Fraction 1 was further purified by gel filtration. 1.5 g of fraction 1 was dissolved in 10 ml 50 mM sodium acetate with pH 4.5 (500 mM KCl). The column is 2.5×100 cm from LKB. The gel filtration filling material is Sephacryl S-200 from Pharmacia, Sweden. The flow rate is 30 ml/hour. The fractions containing materials with molecular weights between 70,000 and 100,000 calibrated with globular proteins, contained an enzyme designated factor G which affects SPS but cannot decompose SPS according to the qualitative agar test; however, SPS is decomposed according to the qualitative agar test when factor G is mixed with a pectinase. It has been found that factor G alone is able to split off galactose, fucose, and some galacturonic acid from SPS. However, the main decomposition product of the SPS according to the HPLC analysis is still a high molecular product very much like SPS.

pH-ACTIVITY DEPENDENCY, TEMPERATURE ACTIVITY DEPENDENCY AND STABILITY OF SPS-ASE

Figure 13:
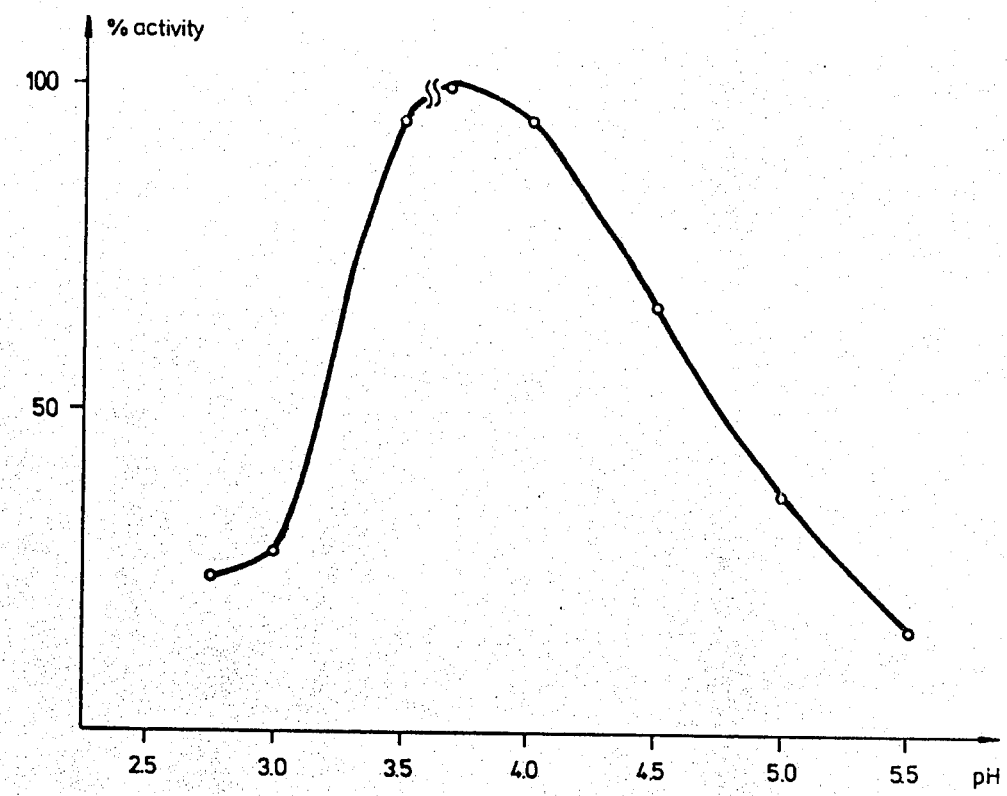
FIG. 13 is the pH activity curve of the same SPS-ase.

FIG. 13 shows the pH activity dependency of the *Aspergillus aculeatus* CBS. 101.43 SPS-ase (preparation KRF 68). From pH 2.7 to pH 3.5 a formic acid buffer system was used, and from pH 3.7 to 5.5 an acetate buffer system was used.

Figure 14:
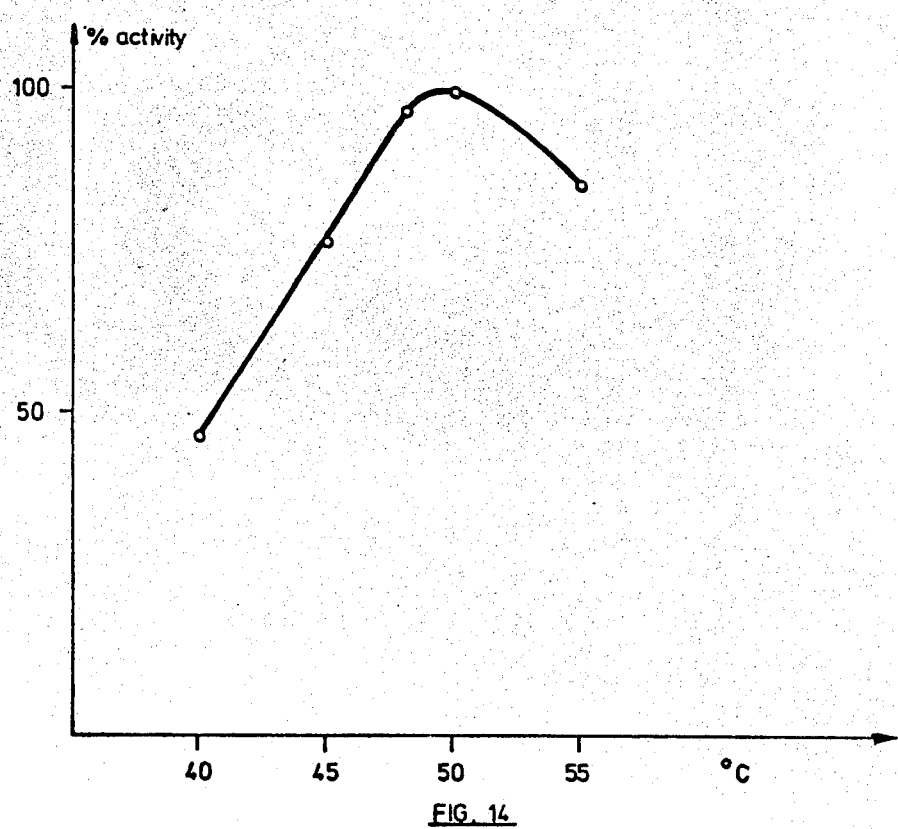
FIG. 14 is the temperature activity curve of the same SPS-ase.

FIG. 14 shows the temperature activity dependency of the SPS-ase preparation KRF 68.

Figure 15:
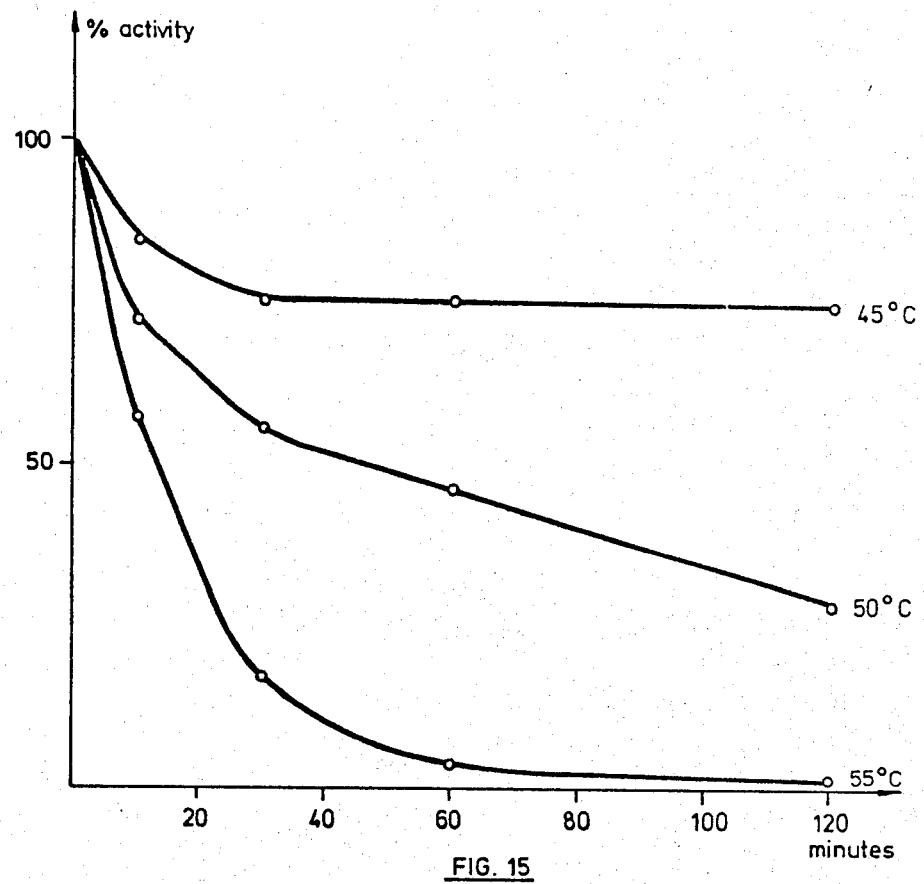
FIG. 15 is the temperature stability curves of the same SPS-ase.
Figure 16:
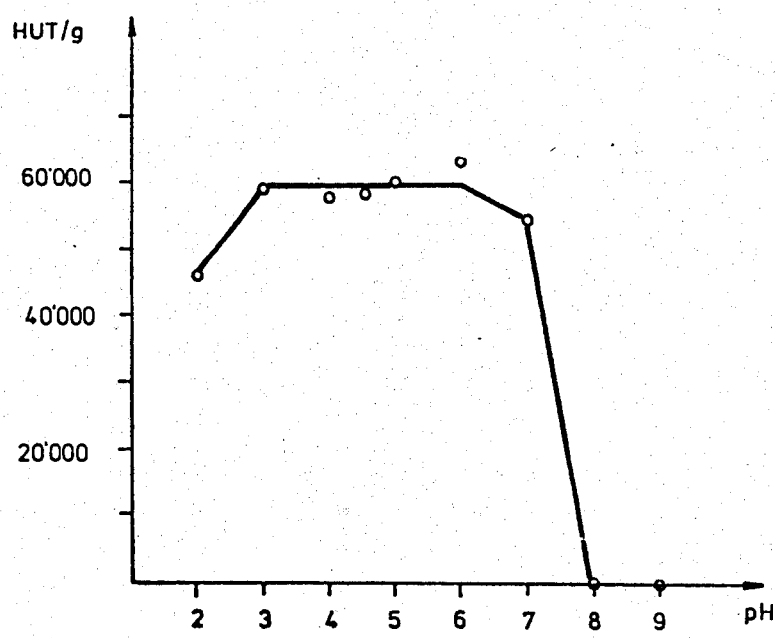
FIG. 16 is the pH-stability curve of the same SPS-ase.

FIG. 15 shows the temperature stability of the SPS-ase preparation KRF 68.

ENZYMATIC ACTIVITY DETERMINATIONS

As has already been pointed out, the SPS-ase of this invention is an enzyme complex containing pectolytic and SPS activity and that other enzyme activities are present in the SPS-ase preparation. For various uses of the SPS-ase preparations the extent of individual activities and of their composite action will often be important. The activities have been measured as is described hereinafter.

The below indicated table is a survey of the different enzymatic activity determinations carried out on SPS-ase preparations of this invention.

| Enzyme | Kind of activity, short designation | Definition of activity unit and description of enzymatic activity determination | | Reference |
|---|---|---|---|---|
| | | Publicly available | Described later in this specification | |
| SPS-ase | SPS-ase | | x | |
| Remanence | SRU | x | | 1 |
| solubilizing | SRUM-120 | | x | |
| Protease | HUT | | x | |
| Cellulase | $C_x$ | x | | 2 |
| Pectinase | PU | x | | 3 |
| | PGE | x | | 4 |
| | UPTE | x | | 5 |
| | PEE | x | | 6 |
| Hemicellulase | VHCU | x | | 7 |

| Reference No | Identification of reference | Reference can be obtained from | | |
|---|---|---|---|---|
| | | NOVO INDUSTRI A/S, Novo Alle, 2880 Bagsvaerd, Denmark | Schweizerische Ferment AG, Basel, Switzerland | A library |
| 1 | Analyseforskrift AF 154/4 of 1981-12-01 | x | | |
| 2 | Analytical Biochemistry 84, 522–532 (1978) | | | x |
| | Analytical method AF 149/6-GB of 1981-05-25 | x | | |
| 3 | Determination of Pectinase Activity with Citrus Pectin (PU) of 23.3.1976 | | x | |
| 4 | Viskosimetrische Polygalacturonase-Bestimmung (PGE) of 10.11.77 | | x | |
| 5 | Bestimmung der Pectintranseliminase (UPTE/g) of 24.Sept.1975 | | x | |
| 6 | Determination of the Pectinesterase activity (undated) with initials WJA/GW | | x | |
| 7 | Analytical method AF 156/1-GB | x | | |

In relation to the cellulase activity determination it can be noted that the analysis was carried out as indicated in AF 149/6-GB and that the principles of the determination is explained in Analytical Biochemistry.

ENZYMATIC DETERMINATION OF SPS-ASE

The enzymatic determination of SPS-ase is carried out in two steps, i.e., a qualitative agar plate test and a quantitative SPS-ase activity determination based on measurement of the amount of total liberated sugars. If the qualitative agar plate test is negative, the SPS-ase activity is zero (regardless of the value originating from the quantitative SPS-ase activity determination if then such test is carried out). If the qualitative agar plate test is positive, the SPS-ase activity is equal to the value originating from the quantitative SPS-ase activity determination.

I. Qualitative agar plate test.

An SPS-agar plate was prepared in the following manner. A buffer (B) is prepared by adjusting 0.3M acetic acid to a pH-value of 4.5 by means of 1N NaOH. 1 g of SPS is dissolved in 20 ml of B. 1 g of agarose (HSB Litex) is mixed with 80 ml of B and heated to the boiling point with stirring. When the agarose is dissolved the SPS-solution is slowly added. The resulting 1% SPS-agarose solution is placed in a water bath of 60° C. The plates are now cast by pouring 15 ml of the 1% SPS-agarose solution on a horizontal glass plate with dimensions 10 cm × 10 cm. The 9 wells with a distance of 2.5 cm are punched out in the solidified layer of SPS-agarose. In each well a 10 $\mu$l sample of a 1% solution of the material to be tested for SPS-ase activity is introduced. The plate is incubated for 18 hours at 50° C. and with a relative humidity of 100%. Then still undecomposed SPS is precipitated by a solution of equal volume parts of ethanol and acetone. The SPS-ase agar plate test is positive for a sample placed in a specific well, if a clear annular zone has appeared around this well.

II. Quantitative SPS-ase activity determination test.

The purpose of this test is the determination of enzymatic activities, which are capable of decomposing SPS to such an extent that the decomposition products exhibit at least greatly reduced binding affinity to soy protein. Experiments have shown that that part of the SPS decomposition products which are not precipitated by a mixture of equal volumes of water and ethanol, do not have any adsorption or binding affinity to soy protein.

The SPS-ase determination is based on a hydrolysis of SPS under standard conditions followed by a precipitation with ethanol of that part of SPS, which is not hydrolyzed. After precipitation the content of carbohydrate still in solution is determined by quantitative analysis for total sugar (according to AF 169/1, available from NOVO INDUSTRI A/S, 2880 Bagsvaerd).

The standard conditions are:
Temperature: 50° C.
pH: 4.5
Reaction time: control 210 minutes with substrate only followed by 2 minutes with added enzyme
Reaction time: main value 212 minutes
The equipment comprises:
Shaking water bath thermostatted at 50° C.
Whirlimixer stirrer
Centrifuge
Ice water bath
The reagents comprise:
Buffer: 0.6M acetic acid in demineralized water (a)
1.0M NaOH (b)
Substrate: The pH value of 50 ml of (a) is adjusted to 4.5 with (b), then 4.0 g SPS are added, and after dissolution of the SPS the pH is readjusted to 4.5, and the volume is adjusted to 100 ml with deionized water.
Stop reagent: Absolute ethanol.

1 SPS-ase activity unit is defined as the SPS-ase activity which under the above indicated standard conditions releases an amount of carbohydrate soluble in 50% ethanol equivalent to 1 μmol galactose per minute.

The initial part of the enzyme standard curve is a straight line; it should be noted that the line does not intersect the (0.0) point.

ANALYTICAL TESTS

ENZYMATIC DETERMINATION OF REMANENCE SOLUBILIZING ACTIVITY EXPRESSED AS SRUM 120

Principle

In the method for determination of hydrolysis activity the insoluble part of defatted, deprotenized, and dehulled soy flour is hydrolyzed under standard conditions. The enzyme reaction is stopped with stop reagent and the insoluble part is filtered off. The amount of dissolved polysaccharides is determined spectrophotometrically after acid hydrolysis according to Z. Dische, Methods of Biochemical Analysis, vol. II pp. 313-323 (1955), Interscience Publ Inc., N.Y. or preferably NOVO INDUSTRI method AF 1691 (available from NOVO INDUSTRI, Bagsvaerd, Denmark).

Carbohydrases with endo- as well as exo-activity are determined according to the method.

The substrate pertaining to this enzymatic determination is identical to the remanence substrate described for the SRU method. The substrate is dissolved as a 3% solution in the below indicated citrate buffer:

0.1N citrate-phosphate buffer pH 4.5

5.24 g citric acid 1-hydrate (Merck Art 244)
8.12 g disodium hydrogen phosphate 2-hydrate (Merck Art. 6580)
Ad 1 l demineralized $H_2O$
pH 4.5±0.05
Stable for 14 days
The stop reagent has the following composition:
 100 ml 0.5N NaOH
 200 ml 96% ethanol
 To be kept in a refrigerator until use.

Standard Conditions

Temperature: 50° C.
pH: 4.5
Reaction time, sample: 120 minutes
Reaction time, blank: 5 minutes Unit Definition One soy remanence solubilizing unit SRUM 120 (M for manual) is the amount of enzyme which, under the given reaction conditions per minute, liberates solubilized polysaccharides equivalent to one micro mole of galactose.

HUT MEASUREMENT

Method for the determination of proteinase in an acid medium.

The method is based on the digestion of denatured hemoglobin by the enzyme at 40° C., pH 3.2, for 30 minutes. The undigested hemoglobin is precipitated with 14% trichloroacetic acid (wt/v%).

All enzyme samples are prepared by dissolving them in 0.1M acetate buffer, pH 3.2.

The hemoglobin substrate is prepared using 5.0 g of lyophilized, bovine hemoglobin powder, preserved with 1% Thiomersalate and 100 ml demineralized water which is stirred for 10 minutes, after which the pH is adjusted to pH 1.7 with 0.33N HCl.

After another 10 minutes of stirring, the pH is adjusted to pH 3.2 with 1N NaOH. The volume of this solution is increased to 200 ml with 0.2M acetate buffer. This hemoglobin substrate must be refrigerated where it will keep for 5 days.

The hemoglobin substrate is brought to room temperature. At time zero, 5 ml of substrate is added to a test tube containing 1 ml of enzyme. After shaking for 1 second, the tube is placed in a 40° C. water bath for 30 minutes. After exactly 30 minutes, 5 ml, 14% trichloroacetic acid is added to the reaction tube, which is then shaken and brought to room temperature for 40 minutes.

For the blank, te hemoglobin substrate is brought to room temperature. At time zero, 5 ml of the substrate is added to a test tube containing 1 ml of enzyme. After shaking for 1 second, the tube is placed in a 40° C. water bath for 5 minutes. After exactly 5 minutes, 5 ml of 14% trichloroacetic acid is added to the reaction tube, which is then shaken and brought to room temperature for 40 minutes.

After 40 minutes, the blanks and samples are shaken, filtered once or twice through Berzelius filter No. 0, and placed in a spectrophotometer. The sample is read against the blank at 275 nm while adjusting the spectrophotometer against water.

Since the absorbance of tyrosine at 275 nm is a known factor, it is not necessary to make a tyrosine standard curve unless it is needed to check the Beckman spectrophotometer.

Calculations

1 HUT is the amount of enzyme which in 1 minute forms a hydrolysate equivalent in absorbancy at 275 nm to a solution of 1.10 microgram/ml tyrosine in 0.006N HCl. This absorbancy value is 0.0084. The reaction should take place at 40° C., pH 3.2, and in 30 minutes.

$$HUT = \frac{Sample - Blank}{0.0084} \times \frac{Vol.\ in\ ml}{reaction\ time\ in\ min.}$$

$$HUT = \frac{Sample - Blank}{0.0084} \times \frac{11}{30} = (S - B) \times 43.65$$

$$HUT/g\ enzyme = \frac{(S - B) \times 43.65}{g.\ enzyme\ in\ 1\ ml}$$

METHOD OF PRODUCING SPS-ASE

The SPS-ase of this invention is produced by fermentation of a SPS-ase producing microorganism strain e.g., the *Aspergillus aculeatus* CBS. 101.43 and *Aspergillus japonicus* IFO 4408.

Surface cultivation or aerobic submerged cultivation techniques, preferably the latter, are contemplated. For example, the microorganism will be cultivated 4–7 days. The SPS-ase appears extracellularly, and may be recovered from the culture broth by conventional enzyme recovery methods, e.g., drum filtration of the broth followed by concentration of the filtrate by evaporation and ultrafiltration or else by salting out of the enzyme.

Known to the art nutrient formulations and cultivation conditions suited for cultivation of *Aspergillus niger* group strains are contemplated.

For best results from cultivation of the above named SPS-ase producer strains, toasted soy meal should be one of the nutrients e.g., 50 g/liter. Also, pectin such as citrus pectin should be added over the course of the fermentation e.g., 10–25 g/liter.

As convenient, any special treatment of the enzyme, for example, deactivation of the proteolytic component may well be carried out during the recovery sequence.

For further understanding of this invention, particularly the aspects thereof relating to SPS-ase and the method of producing SPS-ase the following Example of production of SPS-ase on a pilot plant scale is provided.

EXAMPLE 2

Production of SPS-ase in pilot plant scale

The SPS-ase was prepared by submerged aerobic fermentation of *Aspergillus aculeatus* CBS 101.43.

An agar substrate with the following composition was prepared in a Fernaback flask:

| | |
|---|---|
| Pepton Difco | 6 g |
| Aminolin Ortana | 4 g |
| Glucose | 1 g |
| Yeast extract Difco | 3 g |
| Meat extract Difco | 1.5 g |
| $KH_2PO_4$ Merck | 20 g |
| Malt extract Evers | 20 g |
| Ion exchanged $H_2O$ ad | 1000 ml | pH was adjusted to between 5.30 and 5.35. Then 40 g of Agar Difco was added, and the mixture was autoclaved for 20 min. at 120° C. (the substrate is named E-agar).

The strain CBS 101.43 was cultivated on an E-agar slant (37° C.). The spores from the slant were suspended in sterilized skim-milk, and the suspension was lyophilized in vials. The contents of one lyophilized vial was transferred to the Fernbach flask. The flask was then incubated for 13 days at 30° C.

A substrate with the following composition was prepared in a 500 liter seed fermenter:

| | |
|---|---|
| $CaCO_3$ | 1.2 kg |
| Glucose | 7.2 kg |
| Rofec (corn steep liquor dry matter) | 3.6 kg |
| Soy oil | 1.2 kg |

Tap water was added to a total volume of around 240 liters pH was adjusted to around 5.5 before addition of $CaCO_3$. The substrate was sterilized in the seed fermenter for 1 hour at 121° C. Final volume before inoculation was around 300 liters.

The Fernbach flask spore suspension was transferred to the seed fermenter. Seed fermentation conditions were:

| | |
|---|---|
| Fermenter type: | Conventional aerated and agitated fermenter with a height/diameter ratio of around 2.3. |
| Agitation: | 300 rpm (two turbine impellers) |
| Aeration: | 300 normal liter air per minute |
| Temperature: | 30–31° C. |
| Pressure: | 0.5 ato |
| Time: | Around 28 hours |

Around 28 hours after inoculation 150 liters was transferred from the seed fermenter to the main fermenter.

A substrate with the following composition was prepared in a 2500 liter main fermenter:

| | |
|---|---|
| Toasted Soy Meal | 90 kg |
| $KH_2PO_4$ | 20 kg |
| Pluronic ® | 150 ml |

Tap water was added to a total volume of around 900 liters. The soy bean meal was suspended in water. pH was adjusted to 8.0 with NaOH, and the temperature was raised to 50° C. Thereafter around 925 Anson units of ALCALASE ® 0.6 L was added to the suspension. The mixture was held for 4 hours at 50° C. and pH=8.0 ($Na_2CO_3$ addition) with no aeration, zero ato and 100 rpm agitation. Thereafter the remaining substrate components were added and pH was adjusted to about 6.0 with phosphoric acid. The substrate was sterilized in the main fermenter for 1½ hours at 123° C. Final volume before inoculation was around 1080 liter.

Then 150 liter of seed culture was added.

Fermentation conditions were:

| | |
|---|---|
| Fermenter type: | Conventional aerated and agitated fermenter with a height/diameter ratio of around 2.7. |
| Agitation: | 250 rpm (two turbine impellers) |
| Aeration: | 1200 normal liter air per minute. |
| Temperature: | 30° C. |
| Pressure: | 0.5 ato |
| Time: | Around 151 hours. |

From 24 fermentation hours to around 116 fermentation hours pectin solution was added to the main fermenter at a constant rate of around 8 liters per hour. The pectin solution with the following composition was prepared in a 500 liter dosing tank:

| | |
|---|---|
| Pectin genu[x] | 22 kg |
| Phosphoric acid, conc. | 6 kg |
| Pluronic ® | 50 ml |

[x]Genu pectin (citrus type NF from the Copenhagen pectin factory Ltd.)

Tap water was added to a total volume of around 325 liters. The substrate was sterilized in the dosing tank for 1 hour at 121° C. Final volume before start of dosage was around 360 liters. When this portion ran out, another similar portion was made. Total volume of pectin solution for one fermentation was around 725 liters.

After around 151 fermentation hours the fermentation process was stopped. The around 1850 liters of culture broth were cooled to around 5° C. and the enzymes were recovered according to the following method.

The culture broth was drum filtered on a vacuum drum filter (Dorr Oliver), which was precoated with Hy-flo-super-cel diatomaceous earth (filter aid). The filtrate was concentrated by evaporation to about 15% of the volume of the culture broth. The concentrate was filtered on a Seitz filter sheet (type supra 100) with 0.25% Hy-flo-super-cel as a filter aid (in the following table referred to as filtration I). The filtrate was precipitated with 561 g of $(NH_4)_2SO_4$/l at a pH of 5.5, and 4% Hy-flo-super-cel diatomaceous earth is added as a filter aid. The precipitate and the filter aid are separated by filtration on a frame filter. The filter cake is dissolved in water, and unsoluble parts are separated by filtration on a frame filter. The filtrate is check filtered on a Seitz filter sheet (type supra 100) with 0.25% Hy-flo-supercel as a filter aid (in the following table referred to as filtration II). The filtrate is diafiltered on an ultrafiltration apparatus. After diafiltration the liquid is concentrated to a dry matter content of 12.7% (in the following table referred to as dry matter content in concentrate).

A facultative base treatment for partial removal of the protease activity can be carried out at this stage. In case the base treatment is used it is carried out at a pH of 9.2 for 1 hour, whereafter the pH value is adjusted to 5.0.

Now the liquid is check filtered and filtered for the purpose of germ reduction and the filtrate is freeze-dried on a freeze-drying equipment from Stokes. The best yields from the above described procedure have been about 3 kg of enzyme production per run.

Four fermentations were carried out as described above with the changes indicated below, in the strain used for the fermentation, treatment of the enzyme with base to deactivate proteinase, etc., as indicated in the following table.

carried out for 1 hour. Then pH is reduced to 5.7 with glacial acetic acid. The so obtained material is lyophilized.

| SPS-ase preparation used as starting material for base treatment | Base treatment used A | B | C | Preparation code |
|---|---|---|---|---|
| KRF 68 | x | | | KRF 68 BII |
| KRF 68 | | x | | KRF 68 BIII |
| KRF 92 | | | x | KRF 92 BI |

The activities of the above identified enzyme preparations are provided in the following table.

| Enzyme activity per g | KRF 68 | KRF 68 BII | KRF 68 BIII | KRF 74 | KRF 83 | KRF 92 | KRF 92 BI |
|---|---|---|---|---|---|---|---|
| SAE Plate test | + | + | + | − | + | + | + |
| Quantitative test | 350 | 301 | 349 | 0 | 168 | 476 | 430 |
| SRU | 737 | 507 | 481 | 142 | 683 | 626 | 757 |
| SRUM$_{120}$ | 2125 | 1560 | 1720 | 578 | 753 | 1640 | 1030 |
| HUT pH 3.2 | 67000 | 105 | 339 | 1630 | 12800 | 5960 | 397 |
| C$_x$ | 8000 | 8044 | 9396 | 1320 | 8040 | 5700 | 3092 |
| PU | 10300000 | 9000000 | 8800000 | 840000 | 7500000 | 8400000 | 7600000 |
| PGE | 119400 | 72000 | 77700 | 4100 | 64600 | 60000 | 68800 |
| UPTE | 78100 | 83700 | 76900 | 15130 | 327000 | 44000 | 62400 |
| PEE | 840 | 910 | 770 | 370 | 690 | 1000 | 790 |
| VHCU | 1600000 | 1100000 | 1000000 | 65000 | 2200000 | 1100000 | 742000 |

Reference is now made to the companion application, Ser. No. 339,330, filed concurrently herewith for detailed discussion and exemplification of SPS-ase in production of pvp from vegetable material, particularly from soy meal.

Substrates comparable to SPS are widely found in the plant kingdom associated with or part of plant cell

| Microorganism | Base Treatment used | Base Treatment not used | Preparation code | Concentration (%) of filter aid in connection with filtration I | the precipitation | filtration II | Dry matter content in concentrate | Remarks |
|---|---|---|---|---|---|---|---|---|
| CBS 101.43 | | x | KRF 68 | 0.5 | 5 | 0.2 | 28 | |
| ATCC 20236 | | x | KRF 74 | 2.0 | 4 | 0.4 | 7.5 | |
| IFO 4408 | | x | KRF 83 | 1.0 | 5 | 0.25 | 12.4 | x |
| CBS 101.43 | x | | KRF 92 | 0.25 | 4 | 0.25 | 12.7 | |

$^x$After germ filtration, the filtrate is concentrated by evaporation in a ratio of 1:2.3. A minor part of the concentrated filtrate was spray-dried and remaining part was freeze-dried.

In order to reduce the protease activity still further, some of the above identified SPS-ase preparations were treated as described below by one of the three alternatives A, B and C.

A. 100 g SPS-ase preparation are dissolved in 1 liter of deionized water with stirring at 10° C.±2° C. pH is adjusted to 9.1 with 4N NaOH. This base treatment is carried out for 1 hour. The pH value is then adjusted to 4.5 with glacial acetic acid, and it is dialyzed against ice cold deionized water to a conductivity of 3 mSi. Then freezing and lyophilization are carried out.

B. 500 g SPS-ase preparation are dissolved in 4 liter of deionized water with stirring at 10° C.±2° C. pH is adjusted to 9.1 with 4N NaOH. This base treatment is carried out for 1 hour. The pH value is the adjusted to 5.0 with glacial acetic acid. The so obtained material is lyophilized.

C. 50 g SPS-ase preparation are dissolved in 400 ml of deionized water with stirring at 10° C.±2° C. pH is adjusted to 9.1 with 4N NaOH. This base treatment is walls.

Whenever enzymatic complete disintegration of the cell wall is desired SPS-ase may well be part of the enzyme composition. Qualitative test studies indicate that the enzyme mixture elaborated by the *Aspergillus aculeatus* CBS 101.43 of which SPS-ase is an important portion has liquefied apples and tomatoes. Straw is affected by the enzyme composition to a greater extent than commercially available cellulases, e.g., CELLU-CLAST™.

In the method of processing apples into apple juice wherein pectinase is employed, SPS-ase has evidenced possibilities for being the superior enzyme for the purpose.

We claim:

1. SPS-ase, a carbohydrase complex capable of decomposing the water soluble polysaccharide component of soy remanence that binds to proteins into decomposition products incapable of attaching to protein.

2. The SPS-ase of claim 1 produced by *Aspergillus aculeatus* CBS-101.43.

3. Method for production of SPS-ase, a carbohydrase complex, capable of decomposing the water soluble polysaccharide component of soy remanence that binds to proteins which comprises cultivating a SPS-ase producing microorganism selected from the group consisting of *Aspergillus aculeatus* CPS-101.43, *Aspergillus japonicus* IFO 4408 and mutants thereof in a nutrient medium, followed by recovering the SPS-ase from the cultivation broth.

4. A method according to claim 3, wherein cultivation is carried out by submerged cultivation at a pH in the range of from 3 to 7, at a temperature in the range of from 20° C. to 40° C.

5. A method according to claim 3, wherein the nutrient medium contains toasted soy meal.

6. A method according to claim 5, wherein the soymeal is pre-treated with a proteolytic enzyme.

7. A method according to claim 3, wherein pectin is added to the nutrient medium during the cultivation.

* * * * *